US009884011B2

(12) United States Patent
Bettinger

(10) Patent No.: US 9,884,011 B2
(45) Date of Patent: Feb. 6, 2018

(54) INGESTIBLE, ELECTRICAL DEVICE FOR ORAL DELIVERY OF A SUBSTANCE

(71) Applicant: Carnegie Mellon University, Pittsbrugh, PA (US)

(72) Inventor: Christopher J. Bettinger, Pittsburgh, PA (US)

(73) Assignee: Carnegie Mellon University, Pittsburgh, PA (US)

( * ) Notice: Subject to any disclaimer, the term of this patent is extended or adjusted under 35 U.S.C. 154(b) by 95 days.

(21) Appl. No.: 15/031,418

(22) PCT Filed: Oct. 23, 2014

(86) PCT No.: PCT/US2014/061910
§ 371 (c)(1),
(2) Date: Apr. 22, 2016

(87) PCT Pub. No.: WO2015/061537
PCT Pub. Date: Apr. 30, 2015

(65) Prior Publication Data
US 2016/0263016 A1 Sep. 15, 2016

Related U.S. Application Data

(60) Provisional application No. 61/961,833, filed on Oct. 24, 2013.

(51) Int. Cl.
*A61K 9/00* (2006.01)
*H01M 6/04* (2006.01)
(Continued)

(52) U.S. Cl.
CPC .......... *A61K 9/0009* (2013.01); *A61K 9/0053* (2013.01); *A61K 9/0097* (2013.01);
(Continued)

(58) Field of Classification Search
CPC .. A61K 9/0009; A61K 9/0053; A61K 9/0097; A61K 9/501; A61K 9/5031;
(Continued)

(56) References Cited

U.S. PATENT DOCUMENTS

| 2010/0087885 A1 | 4/2010 | Atanasoska et al. |
| 2010/0239616 A1 | 9/2010 | Hafezi et al. |

FOREIGN PATENT DOCUMENTS

| WO | WO15061537 | 4/2015 |

OTHER PUBLICATIONS

Flieger et al., "Biodegradable Plastics from Renewable Sources", 2003, *Folia Microbiol.* 48 (1), 27-44 (2003), [online], [retrieved on Dec. 30, 2014]. Retrieved from the Internet: <URL: http://www.cssm.info/priloha/FM2003_027.pdf?origin=publication_detail>; paragraphs 2, 4.

(Continued)

*Primary Examiner* — Manuel Mendez
(74) *Attorney, Agent, or Firm* — Fish & Richardson P.C.

(57) ABSTRACT

In one aspect, an ingestible, electrical device, comprises a substrate comprising a reservoir that is configured to hold one or more substances; a first film covering the reservoir, wherein the first film is at least partially metallic; a charge storage system connected to the first film, the charge storage system configured to deliver a transient electrochemical potential to the first film; wherein the first film is configured to prevent exposure of the substance to an aqueous environment in an organism, while the charge storage system delivers the transient electrochemical potential to the first film; and wherein the first film is configured for dissolution to expose the one or more substances to the aqueous environment in the organism, after the charge storage system stops delivering the transient electrochemical potential to the first film.

29 Claims, 4 Drawing Sheets

(51) Int. Cl.
  *H01M 6/32* (2006.01)
  *A61K 9/50* (2006.01)
  *A61K 35/74* (2015.01)
  *H01G 9/14* (2006.01)
  *H01G 9/145* (2006.01)
  *A61K 35/00* (2006.01)

(52) U.S. Cl.
  CPC ............ *A61K 9/501* (2013.01); *A61K 9/5031* (2013.01); *A61K 35/74* (2013.01); *H01G 9/14* (2013.01); *H01G 9/145* (2013.01); *H01M 6/04* (2013.01); *H01M 6/32* (2013.01); *A61K 2035/11* (2013.01)

(58) Field of Classification Search
  CPC ...... A61K 35/74; A61K 2035/11; H01G 9/14; H01G 9/145; H01M 6/04; H01M 6/32
  USPC ..................................................... 604/890.1
  See application file for complete search history.

(56) References Cited

OTHER PUBLICATIONS

Kou et al., "Edible Electronics: A New Trend of Medical Device", (report), May 2014, [online], [retrieved on Dec. 12, 2014]. Retrieved from the Internet: <URL: http://www.epp.cmu.edu/Spring2014Reports/Edible%20Eiectronics%20Final%20Report.pdf>; pp. 5-8.

Shiells, E., "Power-up with Edible Electronics", (news article), Apr. 4, 2013, [online], [retrieved on Dec. 19, 2014]. Retrieved from the Internet: <URL: http://www.rsc.org/chemistryworld/2013/04/edible-polymer-electrode-sodium-ion-electrochemical-cell>; paragraph 3.

International Search Report and Written Opinion dated Jan. 14, 2015 for Int'l. Appln. No. PCT/US14/61910 (10 pgs.).

INGESTIBLE, ELECTRICAL DEVICE FOR ORAL DELIVERY OF A SUBSTANCE

CLAIM OF PRIORITY

This application is a §371 National Stage Application of PCT/US2014/061910, filed Oct. 23, 2014, which, in turn, claims the benefit of priority under 35 U.S.C. §119(e) to provisional U.S. Patent Application No. 61/961,833 filed Oct. 24, 2013, the entire contents of each of which are hereby incorporated by reference.

FIELD OF USE

The present disclosure relates generally to an ingestible, electrical device, and specifically to an electrical device that delivers a substance to the gastrointestinal tract of an organism.

BACKGROUND

Oral delivery systems may control the release of substances to the gastrointestinal tract. Some systems may be designed for controlled release applications where a substance is slowly released in the gastrointestinal tract over a period of time. These systems may not be capable of encapsulating and protecting the substance as the system passes through the stomach. Thus, these systems may not be suitable for orally delivering substances, such as viable bioactive microbial species, to the small intestine. The viability of some microbial species drops to 0% after 60 minutes in a buffer solution having a pH of 2. If the microbial species are not protected while passing through the stomach to the small intestine, some viable microbes may be destroyed in the stomach, which has a pH between 1 and 2.5 and a residence time of greater than 80 minutes. The high acidity and residence time of the stomach may render these orally deliverable substances as non-viable before reaching the small intestine.

Some systems use pH-sensitive polymers that can deliver substances immediately upon entry into the upper gastrointestinal tract, where the pH is approximately 5.8. However, these systems may result in lower viabilities for substances such as anaerobic microbes and may not be suitable for orally delivering these substances to lower downstream portions of the gastrointestinal tract such as the lower small intestine, the large intestine, or the colon.

SUMMARY

The present disclosure describes apparatus and methods relating to an ingestible, electrical device that delivers one or more substances to a gastrointestinal tract of an organism. In one aspect of the disclosure, an ingestible, electrical device comprises a substrate comprising a reservoir that is configured to hold one or more substances; a first film covering the reservoir, wherein the first film is at least partially metallic; a charge storage system connected to the first film, the charge storage system configured to deliver a transient electrochemical potential to the first film; wherein the first film is configured to prevent exposure of the substance to an aqueous environment in an organism, while the charge storage system delivers the transient electrochemical potential to the first film; and wherein the first film is configured for dissolution to expose the one or more substances to the aqueous environment in the organism, after the charge storage system stops delivering the transient electrochemical potential to the first film.

Implementations of the disclosure can include one or more of the following features. The substrate may include a bioexcretable copolymer. The bioexcretable copolymer may include at least one of polyester, polyanhydride, polyamide, polyether, polyphosphoester, polyorthoester, poly(ε-caprolactone) (PCL), or poly(ethylene glycol) (PEG). The ingestible, electrical device may include a second film serving as a counter electrode to the first film, wherein the second film is at least partially metallic, wherein each of the first film and the second film comprises at least one of iron, copper, gold, silver, or manganese, and wherein the first film dissolves at an increased rate, relative to a rate of dissolution of the second film. The first film may prevent exposure of the substance to the aqueous environment for an amount of time that is based on a thickness of the first film and an amount of charge stored in the charge storage device. A thickness of the first film may be less than 150 microns. The charge storage system may be configured to deliver the transient electrochemical potential in reverse bias to the first film. The charge storage system may be configured to deliver the transient electrochemical potential to the first film for a predetermined amount of time based on an amount of charge stored in the charge storage system. The first film may be configured for dissolution to expose the substance to the aqueous environment in the organism in a bolus release manner. The charge storage system may include a water-activated battery comprising one or more non-toxic biocompatible materials. The charge storage system may include a capacitor comprising one or more non-toxic biocompatible materials. The charge storage system may be configured to deliver a transient electrochemical potential greater than 0.5 volts to the first film for at least two hours. The substrate may include another reservoir configured to hold one or more additional substances; a second film may substantially cover the other reservoir; the second film may be configured to prevent exposure of the one or more additional substances to the aqueous environment in the organism, while the charge storage system delivers the transient electrochemical potential to the first film and the second film; and the second film may be configured for dissolution to expose the other substance to the aqueous environment in the organism, after the charge storage system stops delivering the transient electrochemical potential to the first film and the second film. The charge storage system may be connected to the first film using a physical connection.

In another aspect of the disclosure, a method comprises activating, based on exposure to an aqueous environment in an organism, a charge storage system of an ingestible, electrical device, the charge storage system being connected to a first film in the ingestible, electrical device, with a reservoir being covered by the first film, wherein the first film is at least partially metallic; following activation of the charge storage system, delivering a transient electrochemical potential from the charge storage system to the first film; while delivering the transient electrochemical potential from the charge storage system to the first film, preventing dissolution of the first film and exposure of the substance to the aqueous environment in the organism; ceasing to deliver the transient electrochemical potential from the charge storage system to the first film after a predetermined time; and following a cease in delivery of the transient electrochemical potential from the charge storage system to the first film, allowing the first film for dissolution to expose the substance to the aqueous environment in the organism.

Implementations of the disclosure can include one or more of the following features. A substrate may include the reservoir, wherein the substrate may include a bioexcretable copolymer. The bioexcretable copolymer may include at least one of polyester, polyanhydride, polyamide, polyether, polyphosphoester, polyorthoester, poly(ε-caprolactone) (PCL), or poly(ethylene glycol) (PEG). The charge storage system of the ingestible, electrical device is connected to a second film in the ingestible, electrical device that serves as a counter electrode to the first film, wherein the second film is at least partially metallic, wherein each of the first film and the second film comprises at least one of iron, copper, gold, silver, or manganese, and wherein the first film dissolves at an increased rate, relative to a rate of dissolution of the second film. The first film may prevent exposure of the substance to the aqueous environment for a specified amount of time that is based on a thickness of the first film and an amount of charge stored in the charge storage device. A thickness of the first film may be less than 150 microns. The transient electrochemical potential may be delivered in reverse bias to the first film. The predetermined amount of time may correspond to an amount of charge stored in the charge storage system. The first film may be configured for dissolution to expose the substance to the aqueous environment in the organism in a bolus release manner. The charge storage system may include a water-activated battery comprising one or more non-toxic biocompatible materials. The charge storage system may include a capacitor comprising one or more non-toxic biocompatible materials. The transient electrochemical potential may be greater than 0.5 volts and may be delivered for at least two hours. The ingestible, electrical device may include another reservoir for holding another substance, with the other reservoir being covered by a second film, and the method further may include while delivering the transient electrochemical potential from the charge storage system to the first film and the second film, preventing dissolution of the second film and exposure of the other substance to the aqueous environment in the organism; following the cease in delivery of the transient electrochemical potential from the charge storage system to the first film and the second film, allowing the second film for dissolution to expose the substance to the aqueous environment in the organism. The charge storage system may be connected to the first film using a physical connection.

In yet another aspect of the present disclosure, a device for delivering biologically active agents comprises a polycaprolactone substrate comprising a reservoir that is configured to hold a population of biologically active agents; a first film comprising iron and covering the reservoir; a water-activated battery comprising one or more non-toxic biocompatible materials, the water-activated battery connected to the first film, the water-activated battery configured to deliver a transient electrochemical potential greater than 0.5 volts to the first film for at least two hours; wherein the first film is configured to prevent exposure of the population of biologically active agents to an aqueous environment in a stomach of an organism while the water-activated battery delivers the transient electrochemical potential to the first film; and wherein the first film is configured to dissolve and expose the population of biologically active agents to an aqueous environment in an intestine of the organism after the charge storage system stops delivering the transient electrochemical potential to the first film.

The details of one or more implementations are set forth in the accompanying drawings and the description below.

Other features, objects, and advantages will be apparent from the description, the drawings, and the claims.

DETAILED DESCRIPTION

An ingestible, electrical device consistent with this disclosure may include a microfabricated device that can deliver a substance to a specific portion of a gastrointestinal tract of an organism. The device may be orally administered and may reside in the gastrointestinal tract for several hours while protecting the substance from the strongly acidic environment in the stomach. The device can be configured to release the substance in a specific portion of the gastrointestinal tract in a bolus release manner based on an electronic cue that originates from the device without any external (extracorporal) trigger from outside the organism. The electronic cue activates one or more films or membranes to expose the contents contained in one or more reservoirs of the device. The electronic cue may be used to activate dissolution of the films and to control the dissolution rate of the films.

An ingestible, electrical device consistent with this disclosure can have a broad range of potential applications. For example, the device can be used in the treatment of metabolic and immunological diseases that may be caused by unbalanced microbiota populations occurring in a specific portion of the gastrointestinal tract. Microbiota populations in the gastrointestinal tract of a human may affect many aspects of human health, such as proper immunological function and metabolic homeostatis. Imbalanced gut flora, termed dysbiosis, may be a contributing factor to some diseases, such as type 1 and type 2 diabetes mellitus, obesity, inflammatory bowel disease, and atheroschlerosis. Non-pathogenic bacteria are essential components of a healthy metabolism as they aggregate pathogenic bacteria, secrete protective surfactants and enzymes, produce cytokines, serve as immunomodulators, and prevent colonization of pathogenic bacteria. Eubiosis, the healthy state of properly balanced gut microbiota, can limit nutrient uptake and reduce inflammation. Conversely, dysbiosis can contribute to both type 1 and type 2 diabetes by increasing nutrient uptake, insulin resistance, and proinflammatory cytokine profiles.

The device can be used for transplanting viable microbial populations to the specific portion of the gastrointestinal tract to balance microbiota, restore eubiosis, and recover metabolic health. The device may safely and effectively deliver viable probiotics to the intestines for treatment of diabetes, obesity, or both through therapeutic microbiota restoration in a cost-effective and minimally invasive manner. The device may prevent most viable microbes from being destroyed in the stomach, where the pH can be between 1 and 2.5 and the residence time can be greater than 80 minutes. The device can be used to administer synthetically engineered microbes that may exhibit increased pH sensitivity.

Figure 1:
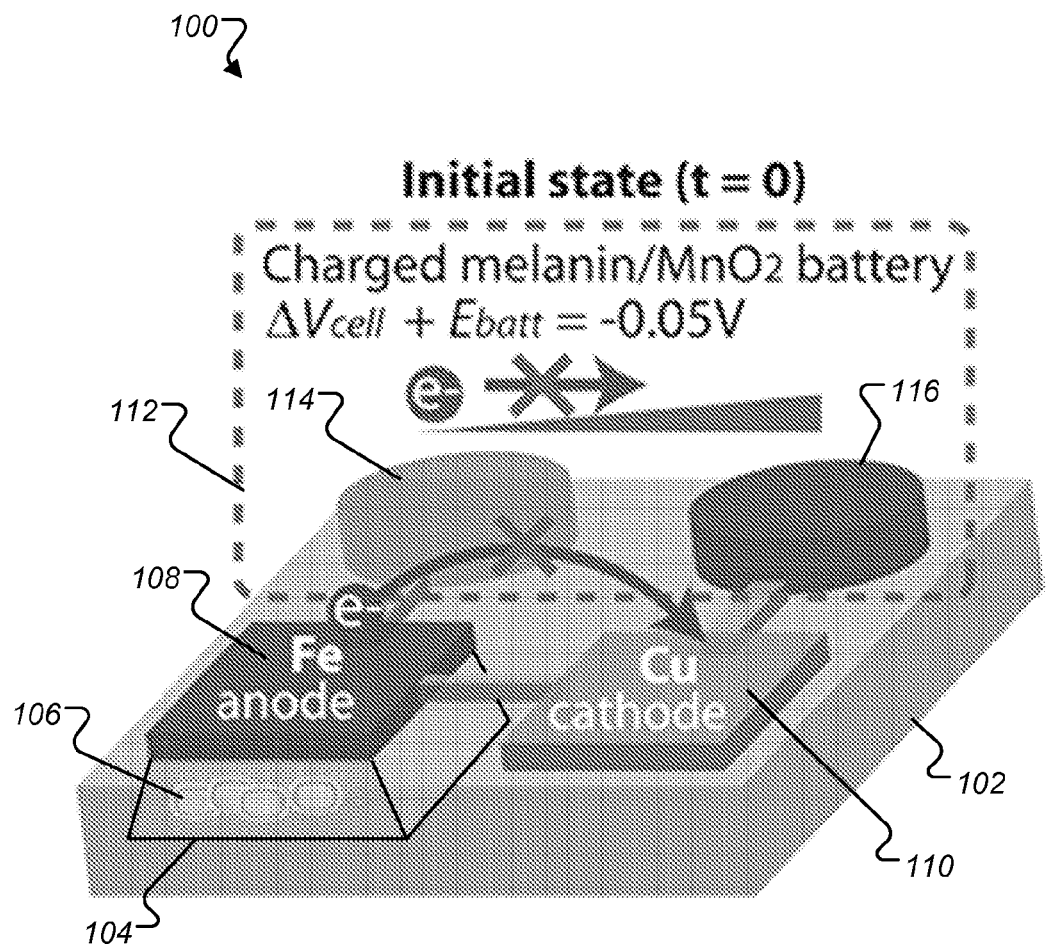
FIG. 1 shows an example of an ingestible, electrical device for delivering a substance to a gastrointestinal tract of an organism.

FIG. 1 shows an example of an ingestible, electrical device 100. The device 100 may be packaged into an orally ingestible capsule that can be self-administered orally to a pediatric or an adult organism. The device 100 includes non-toxic biocompatible materials that can be absorbed, metabolized, or excreted by an organism, e.g., a human or other animal, that ingests the device 100. The device 100 is non-toxic as defined by a maximum concentration that is non-toxic to the organism. The device 100 can deliver a bolus of one or more substances to any portion of the gastrointestinal tract with precise spatiotemporal control.

The device 100 may include a substrate 102. The substrate 102 may include synthetic alpha-hydroxy polymers, cross-linked carbohydrates, polyesters, polyanhydride, polyamides, polyethers, polyphosphoesters, polyorthoesters, poly(ε-caprolactone) (PCL), or poly(ethylene glycol) (PEG). The substrate 102 may be fabricated using, for example, PCL by suitable 3D printing techniques.

The substrate 102 may be fabricated to include a hollow reservoir 104 for holding a substance 106. The substance 106 can include any matter that would need protection from the caustic environment of the stomach as the device transits through the gastrointestinal tract. The substance 106 can include natural or synthetic viable biological matter. For example, the substance 106 can include a microbe composed of any combination of algae, bacteria, fungi, or yeast. As another example, the substance 106 can include biologically active agents such as proteins, antigens, vaccines, and adjuvants. Other examples of an orally deliverable substance include a virus or an eurkaryote. The substance may be loaded into the reservoir using micropipettes.

The reservoir 104 may be covered and sealed with a thin film 108. In some implementations, another thin film 110 may be deposited on the substrate 102 in close proximity to the thin film 108 to serve as a counter electrode, or cathode, to the film 108 to coordinate dissolution (through, e.g., corrosion or erosion) of the film 108, which serves as an anode.

In some implementations, the films 108 and 110 may be micropatterned metallic membranes deposited by thermal evaporation using shadow masks. Each of the films 108 and 110 may be deposited to have a thickness of less than 150 microns. In some implementations, the films 108 and 1100 may be fabricated on handling substrates and transferred to the PCL substrate 102 using microcontact printing.

Each of the films 108 and 110 may be at least partially metallic and include a noble metal such as iron, copper, gold, silver, or manganese, or any suitable combination of noble metals. Materials may be selected for the films 108 and 110 to coordinate galvanic corrosion of the films 108 and 110, with the film 108 corroding at a faster rate than the film 110. For example, the film 108 may include iron, and the film 100 may include copper. The films 108 and 110 may include other suitable materials devised for preprogrammed galvanic corrosion including water diffusion barriers. Electrolytic dissolution of the films 108 and 110 present negligible toxicity profiles to both the substance 106 and the organism ingesting the device 100.

Corrosion rates of the films 108 and 110 may be based on the thickness of the films 108 and 110. The corrosion rate of a thin film (e.g., a film having a thickness less than 150 microns) may be controllable and predictable, but the film alone may only be capable of protecting the substance from exposure on shorter time scales on the order of hours in a reliable time window. The corrosion rate of thicker films may extend the time line for corrosion, but the ability to predict the corrosion rate may become more difficult as the film becomes thicker due to pitting which can lead to uneven corrosion of metallic membranes. Corrosion behavior may also be a challenge to predict in biological environments that have proteins and aqueous solutions with high ionic strengths.

The device 100 may include a charge storage system 112 to control the onset of dissolution of the films 108 and 110. The charge storage system 112 may provide a temporary electrochemical potential in reverse bias to the films 108 and 110 to temporarily stabilize the films 108 and 110. When used in combination with appropriately selected materials for the films 108 and 110, the charge storage system 112 can be used to control the dissolution rate of the films 108 and 110 and program the release time of the substance 106. The exogenous potential supplied by the charge storage system 112 may delay the onset of dissolution of the films 108 and 110 in a predictable manner. Delaying the onset of dissolution of the films 108 and 110 may increase the specificity of the portion of the gastrointestinal tract in which the substance 106 will be released. Coupling the films 108 and 110 with the charge storage system 112 enables the ability to control the dissolution of the films 108 and 110 on long time scales (e.g., 10 to 20 hours). This long time scale may permit the delivery of microbiota, viruses, or other viable organisms to any region within the gastrointestinal tract.

The charge storage system 112 may be composed of non-toxic biocompatible materials that can be absorbed as nutrients or excreted as waste. The substrate 102 may be fabricated to contain relief features for electrodes 114 and 116 of the charge storage system 112. The electrodes 114 and 116 and electrical contacts may be fabricated on handling substrates and transferred to the PCL substrate 102 using microcontact printing. In some implementations, the charge storage system 112 may be a water-activated battery. In some implementations, the charge storage system 112 may be a capacitor or a supercapacitor.

For example, the charge storage system 112 may be a water-activated battery composed of a sodium-loaded melanin anode and a lambda manganese oxide (λ-$MnO_2$) cathode. The electrical potential of melanin λ-$MnO_2$ batteries may be maintained for several hours. The applied potential of melanin batteries drops over time as the anode is discharged. The time ($t_1$) at which the battery can maintain a potential of $|E|>+0.7$ volts can be adjusted by controlling the sodium ($Na^+$) loading. The battery may have sufficient storage capacity to delay the onset of dissolution of the films 108 and 110 for more than two hours ($t_1$). The corrosion time ($t_2$) of the film 108 can be controlled by selecting an appropriate thickness and material for the film 108.

Iron anodes may be stable under an externally applied potential of $|E|>+0.5$ V at a pH ranged of 1 to 9, which is within the range of gastric and intestinal fluids. Copper cathodes may be stable at all projected potentials supplied by the battery and across all pHs observed in the stomach and intestines. The battery's sodium loading and the film's material and thickness can be selected to control the delivery timeline for delivery of the substance 106 to specific portions of the gastrointestinal tract. The anodic and cathodic half-cell reactions for a pair of iron and copper films may be given as follows: $Fe^{2+}(aq)+2e-\rightarrow Fe(s)$ ($E_{anode}=-0.41$ V); $Cu^{2+}(aq)+2e-\rightarrow Cu(s)$ ($E_{cathode}=+0.34$ V). The voltage of the battery cell may be given by $\Delta V_{cell}=E_{cathode}-E_{anode}=0.75$ V. A reverse potential of this amount may confer galvanostatic protection to the iron film. This potential may define the voltage requirements for the charge storage system.

Although FIG. 1 shows the device 100 having one reservoir 104, an ingestible, electrical device may include multiple reservoirs for holding two distinct substances. The film that serves as the cathode, e.g., film 110 of device 100, may also cover and seal a reservoir. The two distinct substances may be released at two different pre-programmed release times. The pre-programmed release times are based on delayed galvanic dissolution of the films, which are stabilized temporarily by applying a transient electrochemical potential in reverse bias. The prescribed charge capacity of the charge storage system determines the delay time before initiating corrosion of the films. The device may be designed for a two-phase release for delivery of one of the substances contained in one of the reservoirs to the upper gastrointestinal tract and the other of the substances contained in another reservoir to the lower gastrointestinal tract. For example, RFP+*E. Coli* bacteria can be delivered to the upper gastrointestinal tract, and GFP *E. Coli* bacteria can be delivered to the lower gastrointestinal tract. The charge storage system can be configured to release one of the substances after two hours following ingestion and the other substance after four hours following ingestion. These two release times may enable targeting of the upper small intestine and the lower small intestine.

Figure 2:
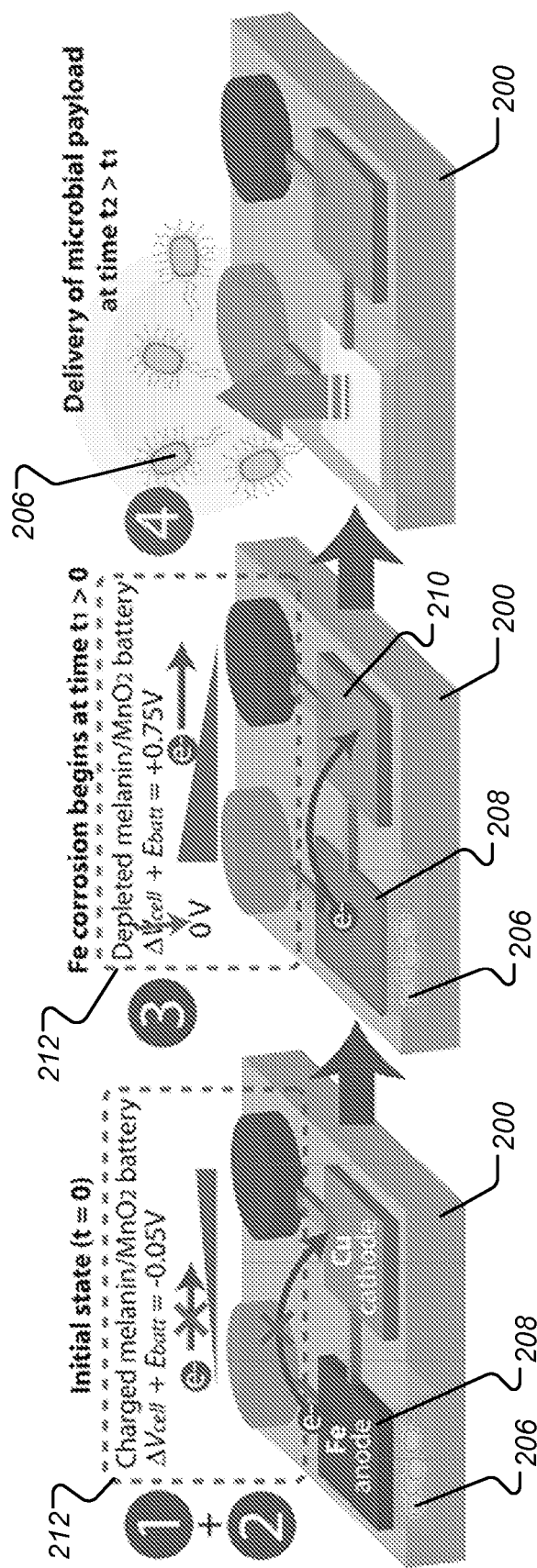
FIG. 2 shows an ingestible, electrical device during different stages of operation.

FIG. 2 shows an ingestible, electrical device 200 during different stages of operation. At stages 1 and 2, a charge storage system 212 supplies a reverse bias that delays corrosion of an iron film 208 for a time period $t_1$ between two and twenty-four hours. After the delay period $t_1$ elapses, galvanostatic corrosion of the iron film 208 and the copper film 210 commences, and the film 208 begins to dissolve at stage 3. At stage 4, a substance 206 is delivered to the gastrointestinal tract of an organism after total dissolution of the film 208 at time $t_2$.

Figure 3:
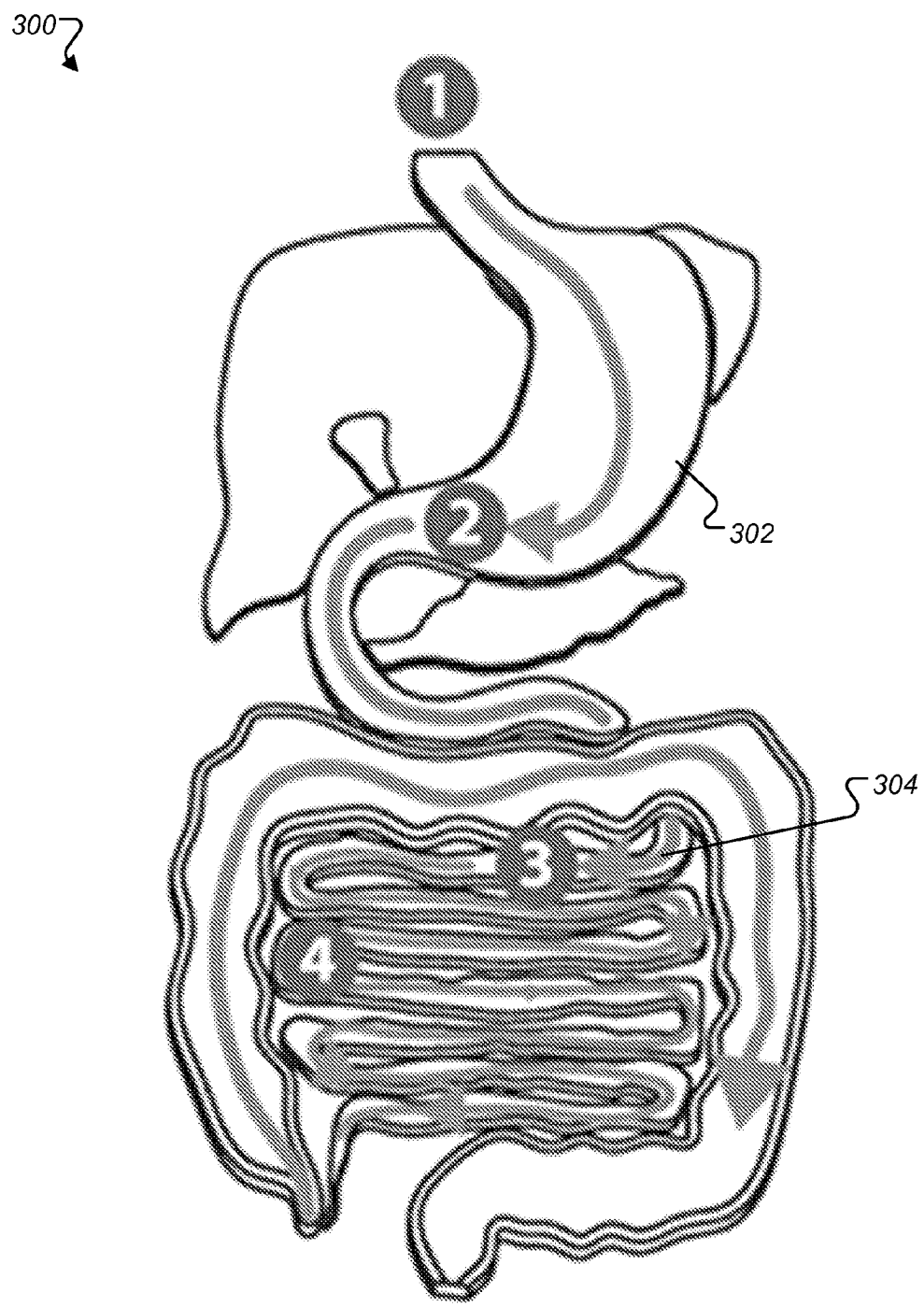
FIG. 3 shows a progression of an ingestible, electrical device through a gastrointestinal tract of an organism.

FIG. 3 shows a progression of an ingestible, electrical device through a gastrointestinal tract 300 of an organism. The organism ingests the device where the device travels from an environment with a pH of 7.2 in the mouth (at position 1) to an environment with a pH of approximately 1 in the stomach 302 (at position 2). The low pH of the stomach 302 does not impact the oxidation potential of the iron film that covers the reservoir. The device will reside in the stomach 302 for approximately 90 minutes before passing to the small intestine 304 (position 3). As the device travels through the small intestine 304, the electrical potential will drop as the battery becomes exhausted (at position 4). Corrosion of the iron film occurs and the substance is delivered after the corrosion time of the film has elapsed.

Figure 4:
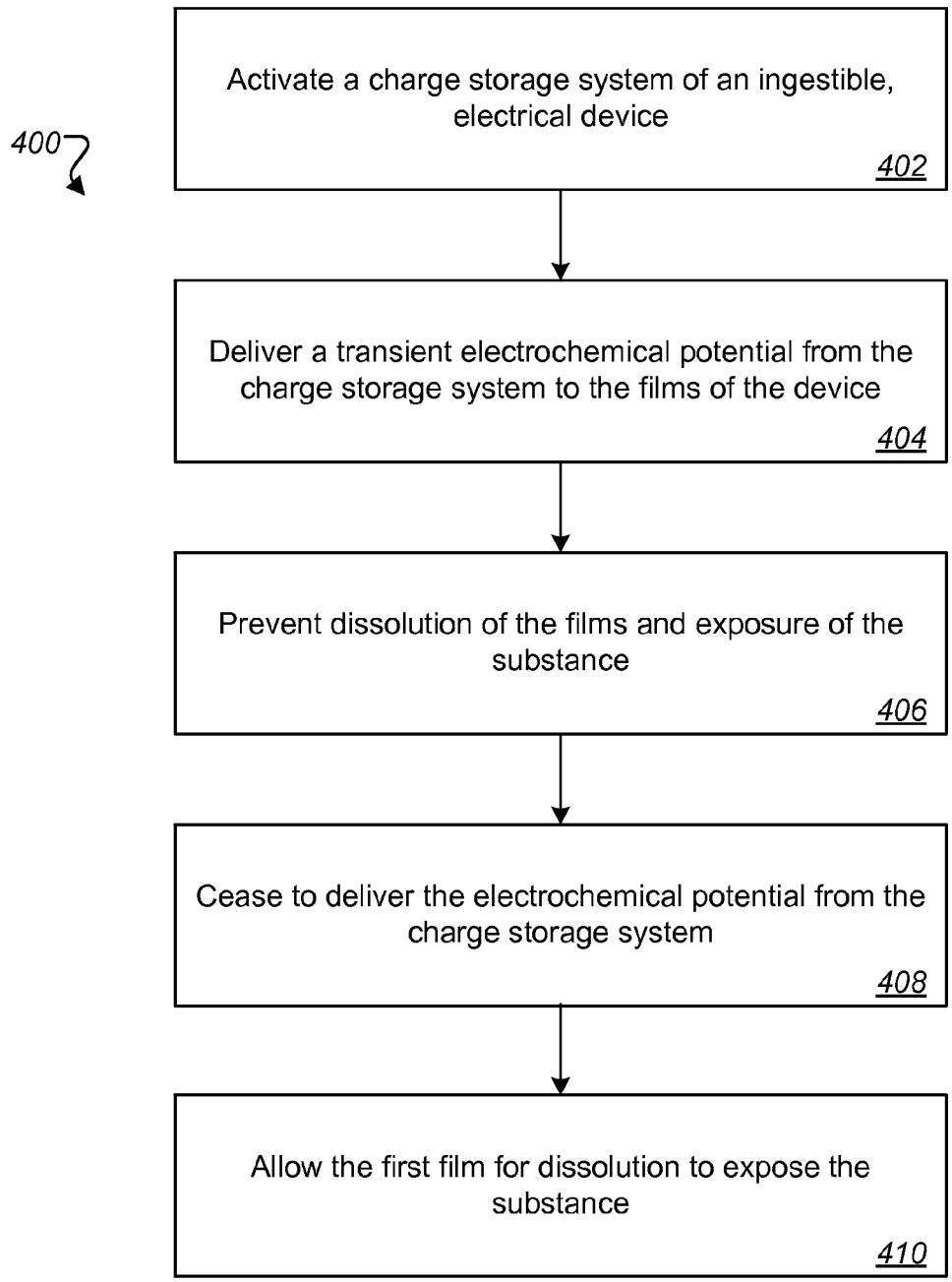
FIG. 4 is a flowchart of operations performed by an ingestible, electrical device to deliver a substance to a gastrointestinal tract of an organism.

FIG. 4 is a flowchart of process 400 performed by an ingestible, electrical device, e.g., the ingestible, electrical device 100 of FIG. 1, to deliver a substance to a gastrointestinal tract of an organism. The operations include activating a charge storage system, e.g., a charge storage system 112 of the device 100 of FIG. 1, of the ingestible, electrical device (402). The activation of the charge storage system may be based on exposure to an aqueous environment in an organism. Following activation of the charge storage system, a transient electrochemical potential is delivered from the charge storage system to a first film, e.g., film 108 of device 100 of FIG. 1, and a second film, e.g., film 110 of device 100 of FIG. 1 (404). While delivering the transient electrochemical potential from the charge storage system to the first film and the second film, dissolution of the first film and exposure of the substance to the aqueous environment in the organism is prevented (406). After a predetermined time corresponding to an amount of charge stored in the charge storage system, the transient electrochemical potential from the charge storage system ceases to be delivered to the first film and the second film (408). Following a cease in delivery of the transient electrochemical potential from the charge storage system to the first film and the second film, the first film is allowed for dissolution to expose the substance to the aqueous environment in the organism (410).

A number of implementations have been described. Nevertheless, various modifications can be made without departing from the spirit and scope of the processes and techniques described herein. In addition, the processes depicted in the figures do not require the particular order shown, or sequential order, to achieve desirable results. In addition, other steps can be provided, or steps can be eliminated, from the described processes, and other components can be added to, or removed from, the describe apparatus and systems. Accordingly, other embodiments are within the scope of the following claims.

What is claimed is:

1. An ingestible, electrical device, comprising:
   a substrate comprising a reservoir that is configured to hold one or more substances;
   a first film covering the reservoir, wherein the first film is at least partially metallic;
   a charge storage system connected to the first film, the charge storage system configured to deliver a transient electrochemical potential to the first film;
   wherein the first film is configured to prevent exposure of the substance to an aqueous environment in an organism, while the charge storage system delivers the transient electrochemical potential to the first film; and
   wherein the first film is configured for dissolution to expose the one or more substances to the aqueous environment in the organism, after the charge storage system stops delivering the transient electrochemical potential to the first film.

2. The ingestible, electrical device of claim 1, wherein the substrate comprises a bioexcretable copolymer.

3. The ingestible, electrical device of claim 2, wherein the bioexcretable copolymer comprises at least one of polyester, polyanhydride, polyamide, polyether, polyphosphoester, polyorthoester, poly(ε-caprolactone) (PCL), or poly(ethylene glycol) (PEG).

4. The ingestible, electrical device of claim 1, further comprising:
   a second film serving as a counter electrode to the first film,
   wherein the second film is at least partially metallic,
   wherein each of the first film and the second film comprises at least one of iron, copper, gold, silver, or manganese, and
   wherein the first film dissolves at an increased rate, relative to a rate of dissolution of the second film.

5. The ingestible, electrical device of claim 1, wherein the first film prevents exposure of the substance to the aqueous environment for an amount of time that is based on a thickness of the first film and an amount of charge stored in the charge storage device.

6. The ingestible, electrical device of claim 1, wherein a thickness of the first film is less than 150 microns.

7. The ingestible, electrical device of claim 1, wherein the charge storage system is configured to deliver the transient electrochemical potential in reverse bias to the first film.

8. The ingestible, electrical device of claim 1, wherein the charge storage system is configured to deliver the transient electrochemical potential to the first film for a predetermined amount of time based on an amount of charge stored in the charge storage system.

9. The ingestible, electrical device of claim 1, wherein the first film is configured for dissolution to expose the substance to the aqueous environment in the organism in a bolus release manner.

10. The ingestible, electrical device of claim 1, wherein the charge storage system comprises a water-activated battery comprising one or more non-toxic biocompatible materials.

11. The ingestible, electrical device of claim 1, wherein the charge storage system comprises a capacitor comprising one or more non-toxic biocompatible materials.

12. The ingestible, electrical device of claim 1, wherein the charge storage system is configured to deliver a transient electrochemical potential greater than 0.5 volts to the first film for at least two hours.

13. The ingestible, electrical device of claim 1, wherein:
the substrate comprises another reservoir configured to hold one or more additional substances;
a second film substantially covers the other reservoir;
the second film is configured to prevent exposure of the one or more additional substances to the aqueous environment in the organism, while the charge storage system delivers the transient electrochemical potential to the first film and the second film; and
the second film is configured for dissolution to expose the other substance to the aqueous environment in the organism, after the charge storage system stops delivering the transient electrochemical potential to the first film and the second film.

14. The ingestible, electrical device of claim 1, wherein the charge storage system is connected to the first film using a physical connection.

15. A method performed by an ingestible, electrical device that comprises a reservoir for holding a substance, the method comprising:
activating, based on exposure to an aqueous environment in an organism, a charge storage system of the ingestible, electrical device, the charge storage system being connected to a first film in the ingestible, electrical device, with the reservoir being covered by the first film, wherein the first film is at least partially metallic;
following activation of the charge storage system, delivering a transient electrochemical potential from the charge storage system to the first film;
while delivering the transient electrochemical potential from the charge storage system to the first film,
preventing dissolution of the first film and exposure of the substance to the aqueous environment in the organism;
ceasing to deliver the transient electrochemical potential from the charge storage system to the first film after a predetermined time; and
following a cease in delivery of the transient electrochemical potential from the charge storage system to the first film, allowing the first film for dissolution to expose the substance to the aqueous environment in the organism.

16. The method of claim 15, wherein a substrate comprises the reservoir, wherein the substrate comprises a bioexcretable copolymer.

17. The method of claim 16, wherein the bioexcretable copolymer comprises at least one of polyester, polyanhydride, polyamide, polyether, polyphosphoester, polyorthoester, poly($\epsilon$-caprolactone) (PCL), or poly(ethylene glycol) (PEG).

18. The method of claim 15, wherein the charge storage system of the ingestible, electrical device is connected to a second film in the ingestible, electrical device that serves as a counter electrode to the first film, wherein the second film is at least partially metallic,
wherein each of the first film and the second film comprises at least one of iron, copper, gold, silver, or manganese, and wherein the first film dissolves at an increased rate, relative to a rate of dissolution of the second film.

19. The method of claim 15, wherein the first film prevents exposure of the substance to the aqueous environment for a specified amount of time that is based on a thickness of the first film and an amount of charge stored in the charge storage device.

20. The method of claim 15, wherein a thickness of the first film is less than 150 microns.

21. The method of claim 15, wherein the transient electrochemical potential is delivered in reverse bias to the first film.

22. The method of claim 15, wherein the predetermined amount of time corresponds to an amount of charge stored in the charge storage system.

23. The method of claim 15, wherein the first film is configured for dissolution to expose the substance to the aqueous environment in the organism in a bolus release manner.

24. The method of claim 15, wherein the charge storage system comprises a water-activated battery comprising one or more non-toxic biocompatible materials.

25. The method of claim 15, wherein the charge storage system comprises a capacitor comprising one or more non-toxic biocompatible materials.

26. The method of claim 15, wherein the transient electrochemical potential is greater than 0.5 volts and is delivered for at least two hours.

27. The method of claim 15, wherein the ingestible, electrical device comprises another reservoir for holding another substance, with the other reservoir being covered by a second film, and the method further comprises:
while delivering the transient electrochemical potential from the charge storage system to the first film and the second film,
preventing dissolution of the second film and exposure of the other substance to the aqueous environment in the organism;
following the cease in delivery of the transient electrochemical potential from the charge storage system to the first film and the second film, allowing the second film for dissolution to expose the substance to the aqueous environment in the organism.

28. The method of claim 15, wherein the charge storage system is connected to the first film using a physical connection.

29. A device for delivering biologically active agents, comprising:
a polycaprolactone substrate comprising a reservoir that is configured to hold a population of biologically active agents;
a first film comprising iron and covering the reservoir;
a water-activated battery comprising one or more non-toxic biocompatible materials, the water-activated battery connected to the first film, the water-activated battery configured to deliver a transient electrochemical potential greater than 0.5 volts to the first film for at least two hours;

wherein the first film is configured to prevent exposure of the population of biologically active agents to an aqueous environment in a stomach of an organism while the water-activated battery delivers the transient electrochemical potential to the first film; and wherein the first film is configured to dissolve and expose the population of biologically active agents to an aqueous environment in an intestine of the organism after the charge storage system stops delivering the transient electrochemical potential to the first film.

* * * * *